(12) United States Patent
Chen et al.

(10) Patent No.: US 8,816,131 B2
(45) Date of Patent: Aug. 26, 2014

(54) METHOD FOR SYNTHESIZING POLYOXYMETHYLENE DIMETHYL ETHERS CATALYZED BY AN IONIC LIQUID

(75) Inventors: Jing Chen, Gansu (CN); Heyuan Song, Gansu (CN); Chungu Xia, Gansu (CN); Zhen Li, Gansu (CN)

(73) Assignee: Lanzhou Institute of Chemical Physics, Chinese Academy of Sciences, Gansu (CN)

( * ) Notice: Subject to any disclaimer, the term of this patent is extended or adjusted under 35 U.S.C. 154(b) by 524 days.

(21) Appl. No.: 13/154,359

(22) Filed: Jun. 6, 2011

(65) Prior Publication Data

US 2011/0288343 A1   Nov. 24, 2011

Related U.S. Application Data

(63) Continuation of application No. PCT/CN2011/072377, filed on Apr. 1, 2011.

(30) Foreign Application Priority Data

May 18, 2010   (CN) .......................... 2010 1 0176791

(51) Int. Cl.
*C07C 41/58* (2006.01)
*C07C 41/50* (2006.01)
*C07C 41/56* (2006.01)

(52) U.S. Cl.
CPC ................. *C07C 41/50* (2013.01); *C07C 41/56* (2013.01)
USPC .......................................................... 568/601

(58) Field of Classification Search
None
See application file for complete search history.

(56) References Cited

U.S. PATENT DOCUMENTS 5,962,702 A    10/1999   Morishita

FOREIGN PATENT DOCUMENTS

| CA | 2581502 A1 | 5/2006 |
|---|---|---|
| CN | 101182367 A | 5/2008 |
| CN | 101665414 A | 3/2010 |
| EP | 1070755 A1 | 1/2001 |
| EP | 1505049 A1 | 2/2005 |
| WO | 2006045506 A1 | 5/2006 |

OTHER PUBLICATIONS

International Search Report and Written Opinion issued on Jul. 7, 2011 for International Patent Application No. PCT/CN2011/072377.

*Primary Examiner* — Rosalynd Keys
(74) *Attorney, Agent, or Firm* — Knobbe, Martens, Olson & Bear, LLP

(57) ABSTRACT

It is related to a method for preparing polyoxymethylene dimethyl ethers by a continuous acetalation reaction of trioxymethylene and methanol or methylal catalyzed by an ionic liquid. The processing apparatus used in the method includes a reaction zone, a separation zone, a catalyst regeneration zone and a product dehydration zone. A manner of circulating tubular reaction is used, resulting in a high external heat exchange efficiency, a simple structure of design and a low investment. A film evaporator is used, realizing a rapid separation and recycling of the light component, with a high separation efficiency. The separation of the catalyst solution from the crude product is simple, thereby realizing the regeneration and recycling of the catalyst.

15 Claims, 1 Drawing Sheet

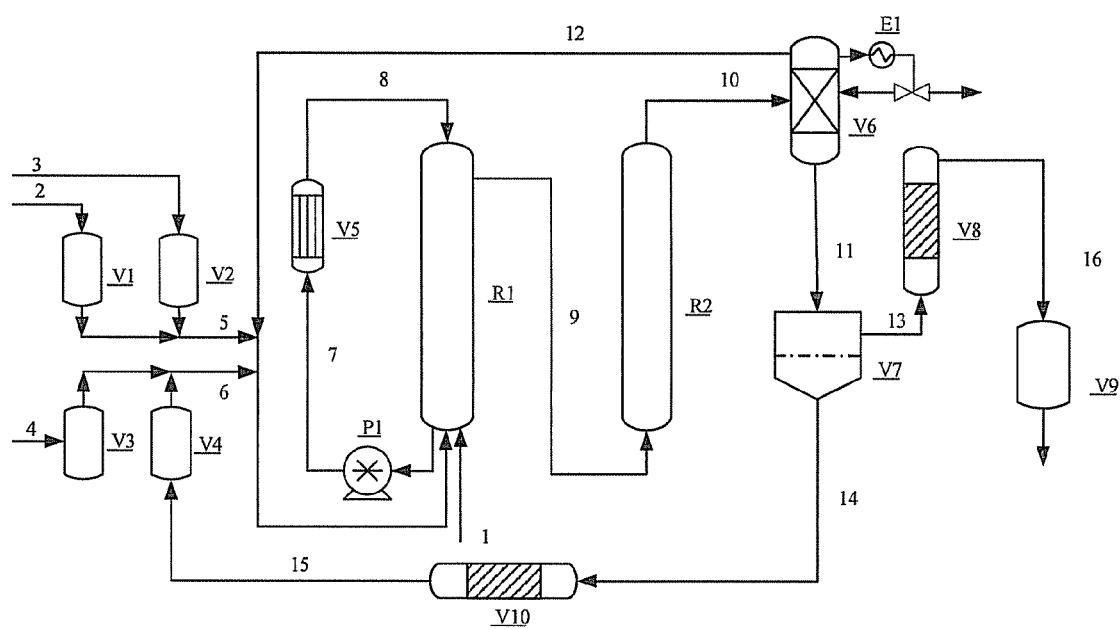

METHOD FOR SYNTHESIZING POLYOXYMETHYLENE DIMETHYL ETHERS CATALYZED BY AN IONIC LIQUID

CROSS-REFERENCE TO RELATED APPLICATION

This application is a Continuation of International Application No. PCT/CN2011/072377, filed Apr. 1, 2011, designating the United States, which claims the benefit of Chinese Application No. 201010176791.5, filed May 18, 2010. The International Application was filed in Chinese and has not been published as of the filing date of the present U.S. National Phase application. The Chinese language application and its associated documents as originally filed in the International Application are hereby incorporated in their entirety.

TECHNICAL FIELD

The present invention relates to a method for preparing polyoxymethylene dimethyl ethers ($H_3CO(CH_2O)_nCH_3$, $DMM_n$, n=2-10) by a continuous acetalation reaction. More specifically, the present invention relates to a method for preparing polyoxymethylene dimethyl ethers by a continuous acetalation reaction of trioxymethylene with methanol or methylal using an ionic liquid as a catalyst.

BACKGROUND ART

Polyoxymethylene dialkyl ethers ($RO(CH_2O)_nR$) are novel blending components for clean oils, which has very high cetane number ($H_3CO(CH_2O)_2CH_3$: 63, $H_3CO(CH_2O)_3CH_3$: 78, $H_3CO(CH_2O)_4CH_3$: 90, $H_3CO(CH_2O)_5CH_3$: 100) and oxygen contents (methyl series: 42%-49%, ethyl series: 30%-43%). When polyoxymethylene dialkyl ethers are added into diesel oil in an amount of 10%-20%, they can improve the burning characteristic of diesel oil remarkably, increase the thermal efficiency effectively, and reduce the discharge of $NO_x$ and carbon smoke greatly, and therefore are regarded as blending components for the environmentally acceptable diesel oils with a promising application prospect. It was reported that when 5%-30% of $H_3COCH_2OCH_3$ was added into diesel oil, the NO content in tail gas could be reduced by 7%-10%, and the particulate pollutants could be reduced by 5%-35%.

In the earlier time, polyoxymethylene dimethyl ethers ($DMM_n$) are synthesized by taking methanol, formaldehyde, paraformaldehyde, or glycol ethylidene-formal as starting material under the catalysis of sulfuric acid or hydrochloric acid. The reaction should be carried out at a relatively high temperature and will produce a great amount of $CO_2$ as byproduct. In 1948, Du Pont (U.S. Pat. No. 2,449,469) investigated the acetalation reaction of polyoxymethylene ether with formaldehyde or paraformaldehyde using an inorganic acidic catalyst such as sulfuric acid under a relatively mild condition, which mainly produced a polyoxymethylene dialkyl ethers wherein n=2-3.

In 2001, Snamprogetti S.P.A. (EP 1070755 A1) reported an acetalation reaction of paraformaldehyde with methylal catalyzed by an inorganic acid such as trifluoromethane sulfonic acid, which was reacted at 115° C./2.0 MPa for 40 min, giving a main product of $DMM_{2-5}$ in a yield of up to 51.2%. Subsequently, the process of the reaction was investigated (EP 1505049 A1). The reaction liquid containing the catalyst was adsorbed on a silica gel column to remove the acid and water. The treated reaction liquid was introduced into a rectification column and separated into light components (trioxymethylene and $DMM_{1-2}$), target products ($DMM_{3-5}$) and heavy components ($DMM_{\geq 5}$) by a two-stage rectification method, wherein the light components and the heavy components were recycled to the reactor for repeated use.

BASF (WO 2006/045506 A1, CA 2581502) reported an acetalation reaction using trioxymethylene as the source of formaldehyde and being catalyzed by protonic acid such as sulfuric acid, trifluoromethane sulfonic acid and acidic cation exchange resin, wherein the reaction was performed at 100° C. for 8-12 h to obtain a series of products wherein n=2-10. The catalyst-containing reaction liquid was adsorbed on a packing column packed with an anion exchange resin to remove the acid and water. The treated reaction liquid was introduced into a rectification column to separate the products by three-stage rectification, wherein the selectivity for $DMM_{3-4}$ is not above 25.7%. The $DMM_n$ with n≤2 and n≥5 was recycled to the reactor for repeated use.

In the above processes of acetalation reaction, the liquid acid catalysts and the products are both in liquid phase, and the catalysts are separated from the reaction liquids by a manner of adsorption or the like. This separation process is complex, and the catalysts cannot be recycled. Additionally, the energy consumption of processing is high. The distribution of products is not desirable and the yield of the component $DMM_{3-8}$ which can be used as an oil additive is not high.

BP Company developed heterogeneous catalyst systems of borosilicate molecular sieve, sulfonic acid-based cation exchange resin or the like (U.S. Pat. Nos. 5,959,156, 6,160,174, 62,655,284). Dimethyl ether and methanol were used as the starting reaction materials to produce formaldehyde via a hydration reaction of dimethyl ether. Further, an acetalation reaction of formaldehyde and methanol produced $DMM_n$. In this reaction process, the separation of the products ($DMM_{\geq 2}$) and the reuse of the raw materials were realized in a reactive rectification manner. However, the catalyst in this method had a low activity and had to be regenerated frequently, leading to a complex process.

In recent years, Lanzhou Institute of Chemical Physics, Chinese Academy of Sciences (U.S. Pat. No. 7,560,599 B2) reported a method for synthesizing $DMM_n$ by an acetalation reaction of trioxymethylene and methanol catalyzed by an ionic liquid, wherein the reaction conversion could be up to 90% and the selectivity for $DMM_{3-8}$ could be up to 40%. The separation and recycling of the catalyst were realized (CN 200810150868.4).

SUMMARY OF INVENTION

An object of the invention is to provide a method for preparing $DMM_n$ by a continuous acetalation reaction of trioxymethylene with methanol or methylal with industrial application value.

The reaction formulas of the invention are:

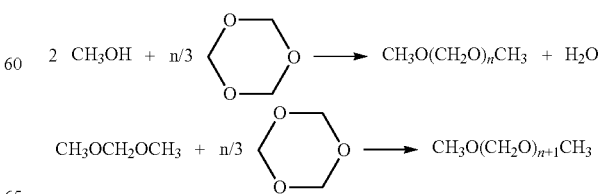

wherein, n is an integer of 1-8.

In the invention, a continuous acetalation reaction wherein trioxymethylene and methanol or methylal are used as starting materials is carried out in a circulating tubular reactor in the presence of an ionic liquid catalyst; subsequently, light components ($DMM_{1-2}$, a part of water, and unreacted methanol and trioxymethylene), target products ($DMM_{3-8}$) and a recycling catalyst solution are separated by a combined separating method of film evaporation and phase separation, and the light components and the treated catalyst solution returned to the reactor to continue catalyzing the reaction.

The processing equipment used in the method of the invention includes a reaction zone, a separation zone, a catalyst regeneration zone and a product dehydration zone.

The invention provides a method for synthesizing polyoxymethylene dimethyl ethers catalyzed by an ionic liquid, including steps of:

A: in a reaction zone including a single-stage or multi-stage tubular reactor and a heat exchanger, continuous acetalation reaction is carried out between trioxymethylene and methanol or methylal using an acidic ionic liquid as catalyst, wherein the reactor and the heat exchanger are connected circularly, and the reaction liquid is circulated in the reactor and the heat exchanger;

B: in a separation zone including a single-stage or multi-stage film evaporator and a phase separator connected in series, allowing the reactor effluent from the reaction zone to drop in pressure, and flow into the film evaporator to be evaporated and condensed, and then introducing the separated liquid phase into the phase separator to obtain two streams, one of a crude product and one of a recycling catalyst solution; and C: in a catalyst regeneration zone, introducing the stream of the recycling catalyst solution from step B into an adsorption tower, and then directing the stream of the recycling catalyst solution treated by the adsorption tower back to the reaction zone for the acetalation reaction.

The method of the present invention further includes a step of:

D: in a product dehydration zone, sending the stream of the crude product from step B to an adsorption tower for a treatment.

According to the method of the invention, in step A, the reaction is carried out continuously at 100-130° C. and under 1.0-5.0 MPa.

According to the method of the invention, the acidic ionic liquid in the reaction zone has a cation portion which is at least one selected from the group consisting of cations of quaternary ammoniums, cations of quaternary phosphines, cations of imidazoles, cations of pyridines and cations of other heterocycles, and an anion portion which is at least one selected from the group consisting of p-toluenesulfonate, trifluoromethyl sulfonate, methyl sulfonate, hydrosulfate, and trifluoroacetate.

According to the method of the invention, in step B, the evaporation and condensation in the film evaporator are carried out under a protection of nitrogen gas.

According to the method of the invention, in step C, the adsorption tower in the catalyst regeneration zone is packed with a cation exchange resin.

According to the method of the invention, in step C, the operating condition of the adsorption tower in the catalyst regeneration zone is 20-100° C.

According to the method of the invention, in step D, the adsorption tower in the product dehydration zone is packed with silica gel or an anion exchange resin.

According to the method of the invention, in step D, the adsorption tower in the product dehydration zone is washed with methanol or methylal to recover the catalyst.

According to the method of the invention, in the reaction zone in step A, in the starting materials the molar ratio of trioxymethylene to methanol or methylal is 0.3-1.6.

According to the method of the invention, the catalyst accounts for 1-5 wt % of all the starting materials.

According to the method of the invention, in the reaction zone, the reaction temperature is 115-120° C.; the reaction system is charged with an inert gas, preferably nitrogen gas or helium gas, with a pressure of 1.0-3.0 MPa; and the residence time of the reaction is 20-60 min. According to the method of the invention, in the separation zone, the film evaporator is selected from a falling film evaporator, a scraper thin film evaporator and a scraper-less thin film evaporator, and the operating conditions thereof include an evaporation temperature of 20-100° C. and a pressure of −0.1--0.01 MPa.

According to the method of the invention, in the product dehydration zone, the operating condition of the adsorption tower is 20-100° C.

The invention provides a method for synthesizing polyoxymethylene dimethyl ethers catalyzed by an ionic liquid, characterized in that the method includes the following steps:

A: in a reaction zone including a single-stage or multi-stage tubular reactor and a heat exchanger, continuous acetalation reaction is carried out between trioxymethylene and methanol or methylal at 100-130° C. and under 1.0-5.0 MPa by using an acidic ionic liquid as catalyst, wherein, the reactor and the heat exchanger are connected circularly, and a reaction liquid is circulated in the reactor and the heat exchanger; the reactor effluent eluted continuously from the reaction zone, in addition to the $DMM_{1-8}$ and water produced, further comprises unreacted starting materials and the catalyst; the acidic ionic liquid has a cation portion which is at least one selected from the group consisting of cations of quaternary ammoniums, cations of quaternary phosphines, cations of imidazoles, cations of pyridines and cations of other heterocycles, and an anion portion which is at least one selected from the group consisting of p-toluenesulfonate, trifluoromethyl sulfonate, methyl sulfonate, hydrosulfate, and trifluoroacetate;

B: in a separation zone including a single-stage or multi-stage film evaporator and a phase separator connected in series, allowing the reactor effluent from the reaction zone to drop in pressure, and flow continuously into the film evaporator to be evaporated and condensed under a protection of nitrogen gas so as to separate a light component, and then continuously introducing the mixed solution of $DMM_{3-8}$, water and the catalyst into a phase separator to obtain two streams, one of a crude product and one of a recycling catalyst solution; wherein the crude product mainly comprises $DMM_{3-8}$, a small amount of water and the residual ionic liquid, and the recycling catalyst solution mainly comprises the ionic liquid, water, a small amount of methanol, and $DMM_{3-8}$;

C: in a catalyst regeneration zone, introducing the recycling catalyst solution from step B into an adsorption tower packed with a cation exchange resin, and after removing water by adsorption, directing it back to the reaction zone for the acetalation reaction; and the operating condition of the catalyst regeneration zone is 20-100° C.;

D: in a product dehydration zone, sending the crude product from step B to an adsorption tower packed with silica gel or an anion exchange resin to remove water and the residual ionic liquid catalyst by adsorption, and washing the adsorption tower in the product dehydration zone with methanol or methylal to recover the catalyst.

In the reaction zone, the starting materials are trioxymethylene and methanol or formal, and the molar ratio of trioxymethylene to methanol is 0.3-1.0; and the molar ratio of trioxymethylene to methylal is 0.3-1.6.

The catalyst of the invention accounts for 1-5 wt % of all the starting materials.

In the separation zone, the evaporation and condensation are carried out under a protection of nitrogen gas, and the separated light components specifically comprise $DMM_{1-2}$, a part of water, unreacted methanol and trioxymethylene.

An example of the cations of quaternary ammoniums of the ionic liquids used in the invention has a structural formula of:

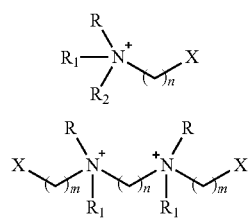

wherein, n and m are integers of 0-15; R, $R_1$, and $R_2$ are straight-chain alkyls with carbon number of 1-6 or a benzene ring; and X is —$SO_3H$, —COOH or a straight-chain alkyl with a carbon number of 1-4.

An example of the cations of quaternary phosphines of the ionic liquids used in the invention has a structural formula of:

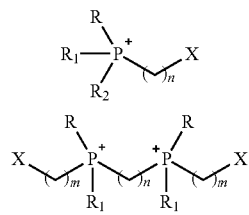

wherein, n and m are integers of 0-15; R, $R_1$, and $R_2$ are straight-chain alkyls with carbon number of 1-6 or a benzene ring; X is —$SO_3H$, —COOH or a straight-chain alkyl with a carbon number of 1-4.

An example of the cations of imidazoles of the ionic liquids used in the invention has a structural formula of:

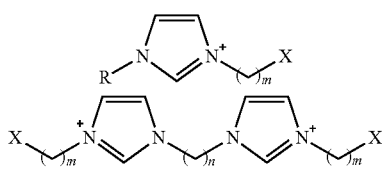

wherein, n and m are integers of 0-15; R is a straight-chain alkyl with a carbon number of 1-6 or a benzene ring; and X is —$SO_3H$, —COOH or a straight-chain alkyl with a carbon number of 1-4.

An example of the cations of pyridines of the ionic liquids used in the invention has a structural formula of:

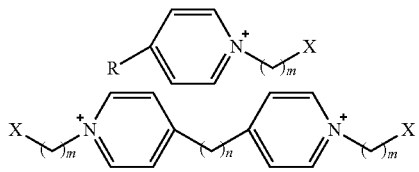

wherein, n and m are integers of 0-15; R is a straight-chain alkyl with a carbon number of 1-6 or a benzene ring; and X is —$SO_3H$, —COOH or a straight-chain alkyl with a carbon number of 1-4.

An example of the cations of heterocycles of the ionic liquids used in the invention has a structural formula of:

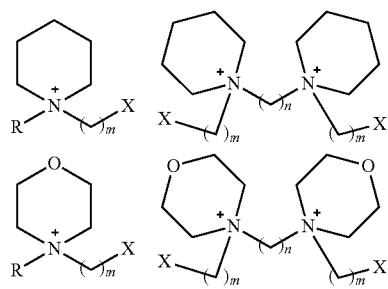

wherein, n and m are integers of 0-15; R is an alkyl or an aryl, preferably, a straight-chain alkyl with a carbon number of 1-6 or a benzene ring; and X is —$SO_3H$, —COOH or a straight-chain alkyl with a carbon number of 1-4.

The examples of the anions of the ionic liquids used in the invention include:

$CH_3PhSO_3^-$, $CF_3SO_3^-$, $CH_3SO_3^-$, $HSO_4^-$, $CF_3COO^-$.

In the reaction zone, the reaction temperature is preferably 115-120° C.; the reaction system is charged with an inert gas, preferably nitrogen gas or helium gas, with a pressure of 1.0-3.0 MPa; and the residence time of the reaction is 20-60 min.

In the separation zone, the film evaporating apparatus is selected from a falling film evaporator, a scraper thin film evaporator and a scraper-less thin film evaporator, and the operating conditions thereof include an evaporation temperature of 20-100° C. and a pressure of −0.1-−0.01 MPa.

In the catalyst regeneration zone, the adsorption tower is packed with a cation exchange resin and the operating condition thereof is 20-100° C.

In the product dehydration zone, the adsorption tower is packed with silica gel or an anion exchange resin, and the operating condition thereof is 20-100° C.

The method of the invention prepares $DMM_n$ in high conversion and selectivity by a continuous acetalation reaction of trioxymethylene with methanol or methylal. The invention has the following advantages:

1. A manner of circulating tubular reaction is used, resulting in a high external heat exchange efficiency, a simple structure of design and a low investment.

2. A film evaporator is used, realizing a rapid separation and recycling of the light components ($DMM_{1-2}$, methanol, and TOX), with a high separation efficiency.

3. The separation of the catalyst solution from the crude product is simple, thereby realizing the regeneration and recycling of the catalyst.

DESCRIPTION OF DRAWING

FIG. 1 is a flow chart of the process of for synthesizing polyoxymethylene dimethyl ethers catalyzed by an ionic liquid. It is only a schematic flow chart for illustration of the invention, and therefore, only necessary apparatuses for explaining the process are indicated, and other indispensable devices, such as meters, gas affluxing apparatuses, pumps, valves, intermediate tanks, etc. are omitted.

SPECIFIC EMBODIMENTS

The content of the invention is further illustrated with the aid of the drawing.

(1) When starting-up or supplementing a catalyst, an ionic liquid catalyst is added into a catalyst storage tank V3 via line 4, and after being transferred to reactor R1 via a pump, it is circulated in the whole system.

(2) Acetalation reaction: the whole system is replaced with $N_2$ or other inert gases, and the oxygen content in the system is below 10 ppm according to a test of the discharged tail gas. A starting material of trioxymethylene enters starting material storage tank V1 via line 2. A starting material of methanol or methylal enters starting material storage tank V2 via line 3. The starting materials are metered by a fluid mass rate meter (not shown) and flow continuously into the acetalation reactor R1 via line 5. The recycled light component flows continuously into the acetalation reactor R1 via line 12. The recycled catalyst solution is metered and flows continuously into the acetalation reactor R1 via line 6. $N_2$ is purified by a purifying unit, and metered and introduced into the reactor RI via line 1. An acetalation reaction takes place at certain temperature and pressure. The reaction liquid discharged from the bottom of reactor R1 is introduced into a heat exchanger V5 via line 7 by pump P1, and then is directed back to reactor R1 via line 8. The reactor and the heat exchanger are connected circularly, and the reaction liquid is circulated in the reactor and the heat exchanger. The reaction liquid discharged from the top of reactor R1 comprises the catalyst, $DMM_{1-8}$, water, and unreacted methanol and trioxymethylene, which is introduced into tubular reactor R2 via line 9, and continues with the acetalation reaction at certain temperature and pressure.

(3) Gas-liquid separation: the reactor effluent from reactor R2 is transferred to a film evaporator V6 via line 10. The separated gas phase comprises $DMM_{1-2}$, a part of water, and unreacted methanol and trioxymethylene, which, a part thereof is cooled via line 12 and directed back to the reaction system, and a part thereof is condensed by condenser E1 with a part of the condensate directed back to V6. The separated liquid phase comprises the catalyst, $DMM_{3-8}$ and water, which is sent to phase separator V7 via line 11.

(4) Separation of the crude product from the catalyst solution: in phase separator V7, the lower layer comprising the ionic liquid catalyst, water and a small amount of $DMM_{3-8}$ is dehydrated and regenerated by adsorption tower V10, and then transferred to catalyst storage tank V4 via line 15 by a pump, and then transferred to reactor R1 via line 6 for repeated use. The crude product in the top layer, which mainly comprises $DMM_{3-8}$, water and a small amount of the ionic liquid catalyst, is transferred to adsorption tower V8 via line 13 by a pump. After removing water and acid therefrom, the crude product is collected into product storage tank V9 via line 16.

The pressures used herein are all gauge pressures.

The catalysts used in the examples are shown as follows:

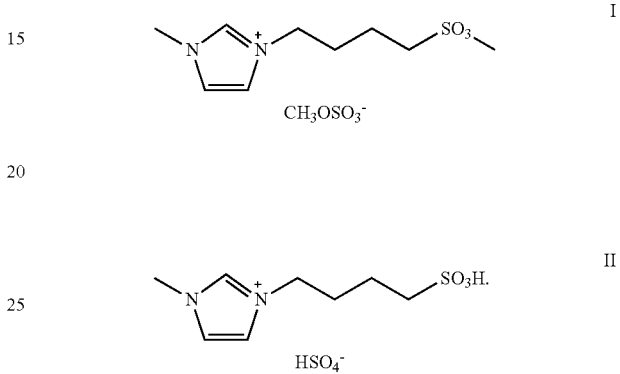

EXAMPLE 1

In the reaction process shown in the drawing, the volumes of reactors R1 and R2 were both 500 mL. Reactor R1 and the heat exchanger were connected circularly, and a reaction liquid was circulated in the reactor and the heat exchanger.

The air in the system was replaced by purging with high purity nitrogen gas. An ionic liquid catalyst I was added into a flowing reaction system at a feeding rate of 0.8 g/min. The feeding was stopped when the catalyst solution began to circulate. The concentration of the catalyst was controlled to be not lower than 4%. Starting materials of trioxymethylene with a purity of 98.5 wt % and methanol with a purity of 99% were added at feeding rates of 11.5 mL/min and 8 mL/min, respectively. The operating conditions for reactors R1 and R2 were controlled to be 115~120° C. and 1.0~2.0 MPa.

The reaction liquid was introduced into film evaporator V6. A light component (comprising $DMM_{1-2}$, and unreacted methanol and trioxymethylene) was separated at 80~95° C. under −0.02 MPa, and directed back to the reaction system. The separated liquid phase was received into phase separator V7 and layers separated at a temperature of 40-60° C. The lower layer, the catalyst solution was transferred back to adsorption tower V10 by a pump to remove water. The water-removed catalyst solution was directed back to the reaction system to continue with the acetalation reaction. The top layer, the crude product was transferred to adsorption tower V8 by a pump to remove water and acid. The water- and acid-removed crude product was allowed to enter product storage tank V9. Samples were taken from the product and the light component at regular time intervals for quantitative analysis by a gas chromatograph. The acetalation reaction was continued for 100 h and the test results were shown in Table 1. In Table 1, all of the flow rates and compositions of substances are average values over the operation of 100 h.

TABLE 1

| Analysis Items | Discharging Rate mL/min | Product Distribution (%) | | | | | | | | | |
|---|---|---|---|---|---|---|---|---|---|---|---|
| | | Methanol | Trioxymethylene | \multicolumn{9}{c|}{$CH_3O(CH_2O)_nCH_3$ with different n values} |
| | | | | 1 | 2 | 3 | 4 | 5 | 6 | 7 | 8 |
| Light Component | 10.5 | 13.3 | 8.9 | 37.6 | 35.9 | 2.4 | 0 | 0 | 0 | 0 | 0 |
| Product | 19.0 | 2.2 | 0.2 | 0 | 0.01 | 27.4 | 26.9 | 19.2 | 12.7 | 7.6 | 4.0 |

The single-pass conversion of trioxymethylene was 93.1%.

EXAMPLE 2

The acetalation reaction was continued for 100 hours in the same manner as example 1, with the exception of adding an ionic liquid II as a catalyst. The average values of the flow rates and compositions of substances were shown in Table 2.

TABLE 2

| Analysis Items | Discharging Rate mL/min | Product Distribution (%) | | | | | | | | | |
|---|---|---|---|---|---|---|---|---|---|---|---|
| | | Methanol | Trioxymethylene | \multicolumn{9}{c|}{$CH_3O(CH_2O)_nCH_3$ with Different n Values} |
| | | | | 1 | 2 | 3 | 4 | 5 | 6 | 7 | 8 |
| Light Component | 9.5 | 12.9 | 10.8 | 38.8 | 37.2 | 1.3 | 0 | 0 | 0 | 0 | 0 |
| Product | 19.0 | 1.7 | 0.2 | 0. | 0.2 | 37.5 | 23.1 | 19.4 | 12.4 | 3.7 | 1.8 |

The single-pass conversion of trioxymethylene was 92.4%.

EXAMPLE 3

The acetalation reaction was continued for 100 hours in the same manner as example 1 except that a single tubular reactor was used. When the feeding rate was unchanged, the residence time was reduced by 50% and the reaction conversion decreased substantially. The average values of the flow rates and compositions of substances were shown in Table 3.

TABLE 3

| Analysis Items | Discharging Rate mL/min | Product Distribution (%) | | | | | | | | | |
|---|---|---|---|---|---|---|---|---|---|---|---|
| | | Methanol | TOX | \multicolumn{9}{c|}{$CH_3O(CH_2O)_nCH_3$ with different n values} |
| | | | | 1 | 2 | 3 | 4 | 5 | 6 | 7 | 8 |
| Light Component | 14.0 | 7.9 | 31.6 | 29.5 | 31.2 | 0.3 | 0 | 0 | 0 | 0 | 0 |
| Product | 18.5 | 1.0 | 0.3 | 0 | 0.6 | 38.5 | 22.6 | 21.4 | 12 | 2.6 | 1.1 |

The single-pass conversion of trioxymethylene was 67.2%.

What is claimed is:

1. A method for synthesizing polyoxymethylene dimethyl ethers catalyzed by an ionic liquid, comprising:
    A: in a reaction zone including a single-stage or multi-stage tubular reactor and a heat exchanger, conducting a continuous acetalation reaction between trioxymethylene and methanol or methylal using an acidic ionic liquid as a catalyst, wherein the reactor and the heat exchanger are connected circularly, and a reaction liquid is circulated in the reactor and the heat exchanger;
    B: in a separation zone comprising a single-stage or multi-stage film evaporator and a phase separator connected in series, allowing the reactor effluent from the reaction zone to drop in pressure, and flow into the film evaporator to be evaporated and condensed, and then introducing the separated liquid phase into the phase separator to obtain two streams, one of a crude product and one of a recycling catalyst solution; and
    C: in a catalyst regeneration zone, introducing the stream of the recycling catalyst solution from B into an adsorption tower, and then directing the stream of the recycling catalyst solution treated by the adsorption tower back to the reaction zone for the acetalation reaction.

2. The method according to claim 1, wherein the method further comprises:
    D: in a product dehydration zone, sending the stream of the crude product from B to an adsorption tower for a treatment.

3. The method according to claim 1, wherein in A, the reaction is carried out continuously at 100-130° C. under 1.0-5.0 MPa.

4. The method according to claim 1, wherein that the acidic ionic liquid in the reaction zone comprises a cation portion which is at least one selected from the group consisting of cations of quaternary ammoniums, cations of quaternary phosphines, cations of imidazoles, cations of pyridines and cations of other heterocycles, and an anion portion which is at least one selected from the group consisting of p-toluene-sulfonate, trifluoromethyl sulfonate, methyl sulfonate, hydrosulfate, and trifluoroacetate.

5. The method according to claim 1, wherein in B, the evaporation and condensation in the film evaporator are carried out under a protection of nitrogen gas.

6. The method according to claim 1, wherein in C, the adsorption tower in the catalyst regeneration zone is packed with a cation exchange resin.

7. The method according to claim 1, wherein in C, the operating condition of the adsorption tower in the catalyst regeneration zone is 20-100° C.

8. The method according to claim 2, wherein in D, the adsorption tower in the product dehydration zone is packed with silica gel or an anion exchange resin.

9. The method according to claim 2, wherein in D, the adsorption tower in the product dehydration zone is washed with methanol or methylal to recover the catalyst.

10. The method according to claim 1, wherein in the reaction zone in A, a molar ratio of trioxymethylene to methanol or methylal as the starting materials is 0.3-1.6.

11. The method according to claim 1, wherein the catalyst accounts for 1-5 wt % of all the starting materials.

12. The method according to claim 1, wherein in the reaction zone, the reaction temperature is 115-120° C.; a reaction system is charged with an inert gas with a pressure of 1.0-3.0 MPa; and the residence time of the reaction is 20-60 min.

13. The method according to claim 1, wherein in the separation zone, the film evaporator is selected from the group consisting of a falling film evaporator, a scraper thin film evaporator and a scraper-less thin film evaporator, and the operating conditions thereof comprise an evaporation temperature of 20-100° C. and a pressure of −0.1--0.01 MPa.

14. The method according to claim 2, wherein in the product dehydration zone, the operating condition of the adsorption tower is 20-100° C.

15. The method according to claim 12, wherein the inert gas is nitrogen gas or helium gas.

* * * * *